United States Patent [19]

Bartsch

[11] 4,119,567

[45] Oct. 10, 1978

[54] VINYL ACETATE CATALYST

[75] Inventor: Raymond C. Bartsch, Wyoming, Ohio

[73] Assignee: National Distillers and Chemical Corporation, New York, N.Y.

[21] Appl. No.: 750,491

[22] Filed: Dec. 14, 1976

Related U.S. Application Data

[63] Continuation-in-part of Ser. No. 641,799, Dec. 18, 1975, abandoned.

[51] Int. Cl.$^2$ .................. B01J 21/04; B01J 23/44; B01J 23/52; B01J 31/04
[52] U.S. Cl. .................. 252/430; 252/466 PT; 560/245
[58] Field of Search .................. 252/466 PT, 430; 260/497 A

[56] References Cited

U.S. PATENT DOCUMENTS

| | | | |
|---|---|---|---|
| 3,190,912 | 6/1965 | Robinson | 260/497 A |
| 3,567,767 | 3/1971 | Yasui et al. | 252/448 X |
| 3,761,513 | 9/1973 | Sennewald et al. | 260/497 A |

FOREIGN PATENT DOCUMENTS 24,873   7/1972   Japan.

*Primary Examiner*—W. J. Shine
*Attorney, Agent, or Firm*—Kenneth D. Tremain

[57] ABSTRACT

A Group VIII novel metal catalyst supported on an alumina carrier having an alumina content greater than 99.0%, a crystalline alpha-alumina content of greater than 96%, a theta-alumina content of less than about 3.0%, a total calcium and magnesium content of less than 750 ppm, a surface area of about 2 to 6 m$^2$/g, an average crush strength of from about 20 to 45 lbs., a bulk density of less than about 1.35 g/cc, and an acetic acid loading of less than about 1.5% in 200 hours. The catalyst generally contains an alkali metal carboxylate activator and optionally a metal such as gold, copper, and the like. The catalyst is particularly useful for the preparation of unsaturated organic esters such as vinyl acetate and allyl acetate by a vapor phase process wherein a gaseous mixture of an olefinic compound, a lower carboxylic acid, and oxygen is contacted with the catalyst.

6 Claims, No Drawings

VINYL ACETATE CATALYST

This is a continuation-in-part application of U.S. Ser. No. 641,799, filed on Dec. 18, 1975, now abandoned.

The present invention relates to a novel supported catalyst composition and to its use in the preparation of unsaturated organic esters. More particularly, the invention pertains to a Group VIII noble metal catalyst such as palladium metal supported on an alumina carrier wherein the alumina has certain prescribed characteristics which permit it to withstand carboxylic acid attack during prolonged use. The supported catalyst composition is especially useful for the manufacture of unsaturated organic esters wherein the catalyst is contacted with a gaseous mixture comprising an olefinic compound, oxygen, and a lower aliphatic carboxylic acid at elevated temperatures and pressures.

BACKGROUND OF THE INVENTION

In recent years there has been considerable commercial interest in the vapor phase process disclosed in U.S. Pat. No. 3,190,912 for the preparation of unsaturated organic esters such as vinyl acetate from olefinic compounds, organic acids, and oxygen. Palladium metal-containing catalysts supported on an alumina carrier have been found to be particularly useful in such a process for the preparation of vinyl acetate from a gaseous mixture of ethylene, acetic acid, and oxygen. The activity and/or stability of such catalyst compositions have been enhanced by the use of various activators including alkali metal acetates, especially sodium and potassium acetate as well as certain metals such as gold and platinum. U.S. Pat. No. 3,190,912 also discloses the manufacture of other unsaturated esters by varying the olefinic compound and carboxylic acid reactants. The preparation of allyl acetate by related processes is further described in U.S. patent specification Ser. No. 330,536 which was published in the *Official Gazette*, page 1640, Jan. 28, 1975, under the trial Voluntary Protest Program.

Despite the improvements in activity and/or stability of the catalyst composition that have been attained heretofore by the use of various activators, the Group VIII noble metal catalyst compositions employed in the vapor phase processes still undergo a gradual loss in activity under prolonged use and consequently require periodic regeneration in order to maintain the desired activity. Methods designed to overcome the loss in catalytic activity are set forth in U.S. Pat. Nos. 3,650,983 and 3,879,311 which are directed to a regeneration procedure for a Group VIII noble metal catalyst, supported on an alumina carrier, used in vapor phase vinyl acetate process.

It has now been found that catalyst activity is not the sole criterion for determining catalyst life, and that the prior proposals to reactivate the catalyst composition by washing techniques or by regeneration will not assure long catalyst life. More specifically, it was found that during use an alumina loss from the catalyst composition takes place at a constant rate and that the alumina carrier exhibits a serious loss of crush strength. Not only is there a marked decrease in the average crush strength, but the percentage of alumina having less than the prescribed minimum crush strength increased dramatically under prolonged use, for example, in the vapor phase synthesis of vinyl acetate. In fact, the loss of crush strength is so significant that the useful life of the Group VIII noble metal catalyst can actually be limited by the decreasing crush strength. It was further determined that the loss of alumina from the carrier and the attendant drop in the physical strength of the carrier were caused by the presence of a lower carboxylic acid in the feed mixture, e.g., acetic acid, in the vinyl acetate vapor phase processes. This acid reacts with the alumina under process conditions to form aluminum salts and in the periodic reactivation, as set forth in U.S. Pat. No. 3,650,983, these salts are removed with the wash liquor. Attempts to overcome this problem by techniques which might stabilize the presently employed alumina carriers against acetic acid attack were unsuccessful. Moreover, efforts to find a more stable carrier were hampered by the lack of knowledge as to those factors which determine whether the catalyst carrier will have the desired stability when in use.

An improved alumina carrier for a catalyst composition employed in the vapor phase synthesis of vinyl acetate is the subject of U.S. Pat. No. 3,567,767. This patent prescribes the use of a high purity alumina, the purity being no lower than 99%, having a surface area of 60 to 150 $m^2/g$. The palladium metal catalyst supported on such an alumina is stated to have an improved and high catalytic activity. Although improved catalyst life ("stability" as defined for the present invention) is mentioned, this advantage is related to the use of low partial pressures of the organic carboxylic acid and oxygen during the synthesis rather than to the improved alumina carrier. The use of low acid partial pressures for synthesis is not recommended, since it not only decreases the production rate but can put the reaction feed gas mixture in the explosive range.

One use of high purity alumina carriers in catalyst compositions for the vinyl acetate vapor phase process are also disclosed in Japanese Patent Publication Nos. 24873, 24874 and 24876 all of which were published on July 7, 1972. These patent publications cover a variety of the so-called "high purity" aluminas and catalysts prepared on these carriers are stated to have improved catalytic activity and/or stability. Thus, for example, Japanese Patent Publication No. 24,873 is concerned with an alumina containing substantially no delta-alumina and of 95% or greater purity. Although both the theta and alpha forms of alumina can be present, the use of an alumina carrier where all the alumina is in alpha form is also described. Furthermore, this patent publication calls for an alumina carrier having a surface area of from 5 to 120 $m^2/g$ and a pore volume of 0.20 to 0.40 cc/g. Japanese Patent Publication No. 24,874 achieves improved catalyst activity in the vinyl acetate synthesis by utilizing as the carrier silica-alumina having an alumina content of from 50 to 95%, a surface area of 10 to 150 $m^2/g$, a pore volume of 0.3 to 0.7 cc/g, and an alpha-alumina content of less than 5%. On the other hand, Japanese Patent Publication No. 24,876 calls for the use of an alumina carrier of 95% or greater purity having a delta-alumina content of 5% or less, a surface area of from 5 to 120 $m^2/g$, a pore volume of 0.20 to 0.40 cc/g, a particle diameter of from 2 to 6 mm, and wherein 90% or more of the palladium metal is located in the area which is up to 10% from the surface of the carrier. Carrier stability under actual process conditions is not mentioned, or implied, in any of the foregoing patents. As previously stated, catalysts of the type described when used in the synthesis process require periodic reactivation or regeneration. During synthesis and reactivation or regeneration these catalysts are exposed to conditions which encourage carrier degradation. Experience has shown that carriers of high purity alumina with a low surface area and a high crystalline alpha-alumina content are most resistant to degradation. For example, carriers containing silica cannot be reactivated according to U.S. Pat. No. 3,650,983 without considerable loss of silica, and carriers containing more than 2 to 5% theta-alumina undergo rapid attack by carboxylic acids which causes swelling of the carrier and plugging of the reactor. Even alpha-alumina undergoes attack by carboxylic acids, but the rate is considerably slower if the alumina crystallites are large (high degree of crystalline alpha-alumina).

Another patent pertaining to a palladium metal-containing catalyst supported on an alumina carrier is U.S. Pat. No. 3,883,442. Here the modified alumina support is prepared by impregnating a high surface area alumina with a boron compound which upon calcination yields $B_2O_3$, drying the impregnated alumina, and then calcining it at a temperature within the range of 675° to 1400° C. The alumina carrier thus prepared has a surface area between about 5 to 100, preferably about 20 to 70 m$^2$/g, and a porosity of about 0.2 to 0.8, preferably 0.3 to 0.7 ml/g. In the preceding patent the addition of the boron compounds is directed toward preventing the conversion of the alumina to the highly crystalline alpha form while maintaining a high surface area. Such an alumina would not meet the carrier requirements set forth in the present invention.

Each of the aforementioned patents emphasize the importance of the method of manufacturing the alumina carrier. The wide variety of proposals in these patents also suggest that the basis for the selection of those alumina carrier physical and chemical properties which would ensure the desired improvement in catalyst life is not readily apparent and furthermore that the selection of the right combination of properties is extremely difficult.

SUMMARY OF THE INVENTION

In accordance with the present invention it has now been found that the catalyst life of an alumina supported Group VIII catalyst composition can be markedly improved provided the alumina carrier has certain very specific characteristics.

More specifically, it has been found that in order to minimize actual alumina loss from the carrier during processing and thereby maintain the necessary crush strength; the crystalline alpha-alumina content of the carrier must be greater than 96%, preferably greater than 98%, the combined or total calcium and magnesium content must be less than about 750 ppm, preferably less than 200 ppm, the surface area must be within the range of from about 2 to 6 m$^2$/g, preferably from about 3 to 4.5 m$^2$/g, an average crush strength of from about 20 to 45 lbs., and a bulk density of less than about 1.35 g/cc. With an alumina having these characteristics, the carboxylic acid loading will be less than about 1.5 in 200 hours, preferably less than about 1% in 200 hours, and the ability of the alumina carrier to resist carboxylic acid attack will be enhanced.

The alumina carrier of this invention is designed to be employed in conjunction with Group VIII noble metals, and generally in conjunction with alkali metal or alkaline earth metal carboxylate activators, preferably alkali metal acetates. The Group VIII nobel metal-containing catalyst may optionally contain other metals such as metals from Groups V to VIII of the Periodic System or salts thereof. It will be understood that other activators and promoters may be employed with the Group VIII noble metals, and that other catalytic metals, either alone or admixed with the Group VIII noble metals, may be supported on the alumina carrier.

As previously set forth, the alumina supported catalysts of the present invention have been found to be especially applicable in processes relating to the manufacture of unsaturated organic esters by the oxyacetylation of olefinic compounds. The preparation of vinyl acetate by the vapor phase procedure described in U.S. Pat. No. 3,190,912, the disclosure of which is incorporated herein by reference, is one of the important commercial processes wherein the alumina supported catalysts can be effectively utilized. Another process involves the reaction of propylene with acetic acid in the presence of oxygen to form allyl acetate.

For the purposes of this invention the following definitions are given: (1) "alumina purity" means the weight percent aluminum oxide in the carrier, (2) "catalyst activity" (or activity) is the rate at which the catalyst yields the desired product, (3) "catalyst stability" refers to the ability of the catalyst to maintain a certain level of activity over long periods of time, and (4) "catalyst life" refers to the length of time over which the catalyst maintains stability. As will become clear in the following discussion, catalyst life includes carrier stability which is the ability of the carrier to resist degradation when the catalyst is used under process conditions.

DETAILED DESCRIPTION OF THE INVENTION

The specifications for the alumina carrier of this invention are as follows:

| | Broad Range | Preferred Range |
|---|---|---|
| Alumina, wt.% | >99 | >99.5 |
| Theta Alumina wt.% | <3 | <1.5 |
| Crystalline Alpha Alumina, wt. % | >96 | >98 |
| Total Calcium plus Magnesium, ppm | <750 | <200 |
| Surface Area, m$^2$/g | 2–6 | 3–4.5 |
| Bulk Density, g/cc | 1.35 max. | 1.30 max. |
| Crush Strength, Avg. lbs. | 20–45 | 23–33 |
| Acid* Loading | | |
| (20 hrs.), wt. % | <0.75 | <0.5 |
| (72 hrs.), wt. % | <1.0 | <0.75 |
| (200 hrs.), wt. % | <1.5 | <1.0 |

*Acetic Acid

The high purity crystalline alpha-alumina carrier utilized in formulating the catalyst compositions of this invention may also contain very minor amounts of metal impurities such as iron, titanium, antimony, arsenic, chromium copper, lead and the like. In general, the other metal impurities are present in total amounts which do not exceed about 1500 ppm. High purity alpha-alumina carrier particles which meet the aforedescribed specifications are available commercially from the Harshaw Chemical Company. The alpha-alumina particles may be in the form of spheres, prills, beads, extrudates, rings, irregular granules, and the like.

The bulk density of the alpha-alumina carrier particles is measured by weighing the amount of sample required to fill a 100-ml. graduated cylinder under specified conditions. The packed bulk density is reported as g./cc.

The lower carboxylic acid or acetic acid loading on the alumina carrier is measured by exposing a dry sample to acetic acid vapor at a pressure of approximately 2.5 atmospheres at 150° C. and then drying the sample to constant weight. The gain in weight is reported as a percentage of the final weight (carrier plus acid). This test determines the amount of acid which actually reacts with the carrier and not that which is physically absorbed.

The alumina loss is measured by determining the weight lost by an acetic acid loaded sample after the sample is washed with a solution of potassium hydroxide and potassium acetate, rinsed with distilled water and dried to constant weight. The weight loss is reported as a percentage of the original, unloaded sample.

The crush strength of the alumina carrier is measured by applying a measurable, steadily increasing force to a single particle held between two flat parallel plates and noting the weight where the particle cracks. The procedure is repeated for a number of particles, and the "crush strength" of the carrier is reported as the average crushing weight required. When the crushing force is applied through an air cylinder with a one-square inch piston, the crushing force is read directly from a suitably connected pressure gauge.

Group VIII noble metal catalysts may be applied to the high purity alpha-alumina carrier by known methods such as those described in U.S. Pat. Nos. 3,655,747 and 3,822,308. Although palladium metal is the preferred catalytic material, other Group VIII noble metals such as platinum, rhodium, ruthenium, and irridium or salts thereof may be employed by themselves or in combination with the palladium metal. It is also generally preferred to apply alkali metal or alkaline earth metal carboxylate activators, having from 2 to 4 carbon atoms, to the carrier. The formates and acetates, and preferably the latter, of sodium, potassium and lithium have been found to be especially advantageous for this purpose. In general, the amount of Group VIII noble metal employed will range from about 0.1 to 10% by weight, preferably between about 0.5 to 2.0%, based on the total weight of catalyst composition. The amount of alkali metal or alkaline earth metal carboxylates employed will range from about 0.01 to 20% by weight, preferably about 0.5 to 10% by weight, based on the total weight of the catalyst composition.

As previously set forth, the catalyst compositions of this invention may also contain other metals such as gold, copper, zinc, cadmium, tin, lead, bismuth, antimony, vanadium, iron, cobalt, manganese, titanium, tellurium, molybdenum, aluminum, chromium, or salts thereof, and the like. The amounts of these other metals utilized may range from about 0.01 to 2% weight, preferably 0.05 to 0.6%, based on the total weight of the catalyst composition.

In accordance with one feature of the present invention the aforedescribed catalyst compositions have been found to be particularly useful in the vapor phase process for the preparation of unsaturated organic esters by the reaction of an aliphatic monolefinic compound, having from 2 to 4 carbon atoms, with a lower aliphatic monocarboxylic acid, having from 2 to 4 carbon atoms, and oxygen at temperatures ranging from about 50° to 300° C., and pressures ranging from normal up to 200 atmospheres, preferably 2 to 20 atmospheres. The preferred olefinic compounds are ethylene, propylene and butenes; and the preferred aliphatic carboxylic acids are acetic acid, propionic acid, butyric acid and isobutyric acid. The oxygen component may be molecular oxygen or an oxygen-containing gas such as air. Although not critical for the present purposes, the molar ratio of the olefinic compound to oxygen may vary from about 80:20 to 98:2, while the molar ratio of the lower carboxylic acid to the olefinic compound may vary from about 1:1 to 1:100.

In the manufacture of vinyl acetate the gaseous feed mixture will comprise ethylene, acetic acid and oxygen. For allyl acetate, on the other hand, the gaseous feed mixture will comprise propylene, acetic acid and oxygen. It will be further understood that the catalyst compositions of this invention are also applicable to process where cycloaliphatic or aromatic compounds are reacted with monocarboxylic acids including those having greater than 4 carbon atoms to prepare unsaturated organic esters.

"Crystalline" alpha alumina, as that term is used in the specification and claims, refers to alpha alumina crystallites of at least about 50 A in diameter, determined relative to a reference standard utilizing conventional X-ray diffraction analysis techniques, and a diffraction angle ($2\theta$) of 25.5°. The reference standard may conveniently be fully crystallized, e.g., alpha alumina formed by hydrolysis of aluminum isopropoxide in water calcined at 1300° C. for 24 hours and evidencing no further crystalline order modification with further calcination at the same temperature. The foregoing is based on the ISO method [ISO/TC 74/WG8 document 351—International Organization for Standardization Technical Committee ISO/TC 47 Chemistry Working Group 8-Alumina—Title: Analysis of Alumina Determination of Alpha Alumina by X-ray Diffraction July 1967].

The invention will be more fully understood by reference to the following illustrative embodiments.

EXAMPLE 1

A series of alumina carriers A through F were analyzed to determine their purity as well as alpha- and theta-alumina content. The results of these analyses and the physical characteristics of each of the aluminas are set forth in the following Table. The aluminas were subjected to the acid loading test, as described above, with acetic acid to determine the percentage of acid loading and the percentage of alumina lost by acid attack. The data in the Table show that higher acid loadings and higher alumina losses can be expected if the sample contains more than 200 ppm Ca plus Mg and/or a surface area greater than $4 m^2/g$ and/or a crystalline alpha-alumina content of less than 98%.

TABLE A

| | Alumina Catalyts Carriers | | | | | | |
| --- | --- | --- | --- | --- | --- | --- | --- |
| | A | B | C | D | E | F | G |
| $Al_2O_3$, wt. % | 99.46 | 99.36 | 99.75 | 99.68 | 99.70 | 99.57 | 99.78 |
| Crystalline Alpha $Al_2O_3$, wt. % | 93.5 | 96.5 | 99.0 | 90.5 | 99.8 | 98.4 | 99.0 |
| Theta $Al_2O_3$, wt. % | 0 | 2.9 | 1.0 | 0 | 0 | 0 | 1.0 |
| Total Calcium + Magnesium, ppm | 2800 | 3600 | 110 | 110 | 130 | 120 | 110 |
| Surface Area, $m^2/g$ | 5.6 | 5.7 | 3.3 | 4.3 | 3.3 | 4.0 | 3.5 |
| Apparent Bulk Density, g/cc | 1.16 | 1.17 | 1.20 | 1.27 | 1.31 | 1.29 | 1.29 |
| Initial Crush Strength - Avg., lbs. | 24.2 | 27.5 | 23.5 | 31.2 | | 27.8 | 45.0 |
| Acetic Acid Loading (20 hrs.), wt. % | 0.73 | 0.87 | 0.35 | 0.58 | 0.25 | 0.32 | 0.42 |

TABLE A-continued

| | Alumina Catalyts Carriers | | | | | | |
|---|---|---|---|---|---|---|---|
| | A | B | C | D | E | F | G |
| Acetic Acid Loading (72 hrs.), wt. % | 1.90 | 2.57 | 0.54 | 1.17 | 0.40 | 0.43 | 0.69 |
| Acetic Acid Loading (200 hrs.), wt. % | 3.62 | 5.08 | 0.86 | 1.84 | 0.48 | 0.52 | 0.94 |
| $Al_2O_3$ Loss after 200 hr. Loading, wt.% | 1.60 | 1.75 | 0.20 | 0.61 | 0.19 | 0.17 | 0.39 |

EXAMPLE II

Alumina carriers A, B, F and G were employed to form vinyl acetate catalysts which were subjected to the 200 hour acid loading and alumina loss tests. The catalyst compositions and test results are given in the following Table:

TABLE B

| | Weight Percent | | 200 Hour Test | |
|---|---|---|---|---|
| Carrier | Palladium | Gold | Acid Loading | Alumina Loss |
| A | 1.25 | 0.55 | 2.01 | 1.26 |
| B | 1.25 | 0.55 | 2.32 | 1.15 |
| F | 1.12 | 0.45 | 0.44 | 0.27 |
| G | 1.08 | 0.45 | 0.63 | 0.20 |

After the addition of 2.5% by weight of potassium acetate all the catalysts were used in the vapor phase process for producing vinyl acetate by contacting them with a gaseous mixture of ethylene acetic acid and oxygen at a temperature of 125° C. and a pressure of 50 PSIA. After 200 hours the yield of vinyl acetate/gram of palladium was 13.3, 13.2, 12.3 and 13.2 for catalysts on carriers A, B, F and G respectively.

The above data show that catalysts prepared on the carrier of the present invention have excellent activity and greatly improved resistance to attack by acetic acid thereby assuring a longer physical life for the catalyst. Moreover, use of this carrier permits operation at higher partial pressures of acetic acid.

While particular embodiments of this invention are shown above, it will be understood that the invention is obviously subject to variations and modifications without departing from its broader aspects.

What is claimed is:

1. A supported catalyst composition for the preparation of unsaturated organic esters from a olefinic compound, oxygen and a lower carboxylic acid in the vapor phase, the catalyst containing from about 0.5 to 2.0% by weight palladium metal, and wherein the catalyst is supported on alumina having a crystalline alpha-alumina content of greater than about 96%, a theta-alumina content of less than about 3%, a total calcium and magnesium content of less than about 750 ppm, a surface area of from about 2 to 6 $m^2/g$, an average crush strength of from 20 to 45 lbs, a bulk density of less than about 1.35 g/cc, and an acetic acid loading of less than about 1.5 in 200 hours.

2. The catalyst composition of claim 1 wherein said catalyst composition additionally contains gold metal.

3. The catalyst composition of claim 1 wherein the catalyst contains from about 0.5 to 10% by weight of an alkali metal acetate.

4. The catalyst composition of claim 3 wherein said alkali metal acetate is sodium acetate.

5. The catalyst composition of claim 3 wherein said alkali metal acetate is potassium acetate.

6. The catalyst composition of claim 1 wherein said lower carboxylic acid is acetic acid.

* * * * *

UNITED STATES PATENT OFFICE
CERTIFICATE OF CORRECTION

PATENT NO. : 4,119,567
DATED : October 10, 1978
INVENTOR(S) : Raymond C. Bartsch It is certified that error appears in the above-identified patent and that said Letters Patent are hereby corrected as shown below:

Add the following claim:

7. The catalyst composition of claim 1, wherein the total calcium and magnesium content is less than about 200 ppm.

Signed and Sealed this

Fourteenth Day of October 1980

[SEAL]

Attest:

SIDNEY A. DIAMOND

Attesting Officer

Commissioner of Patents and Trademarks